(12) United States Patent
Phull et al.

(10) Patent No.: US 11,267,798 B2
(45) Date of Patent: Mar. 8, 2022

(54) PROCESS FOR THE PREPARATION OF PIPERINE

(71) Applicant: CIPLA LIMITED, Mumbai (IN)

(72) Inventors: Manjinder Singh Phull, Mumbai (IN); Dharmaraj Ramachandra Rao, Thane (West) (IN); Geena Malhortra, Mumbai (IN); Dilip Ramdas Birari, Thane (West) (IN); Sachin Vasant Desai, Mumbai (IN)

(73) Assignee: CIPLA LIMITED, Mumbai (IN)

( * ) Notice: Subject to any disclaimer, the term of this patent is extended or adjusted under 35 U.S.C. 154(b) by 63 days.

(21) Appl. No.: 16/765,393

(22) PCT Filed: Oct. 13, 2018

(86) PCT No.: PCT/IN2018/050657
§ 371 (c)(1),
(2) Date: May 19, 2020

(87) PCT Pub. No.: WO2019/073491
PCT Pub. Date: Apr. 18, 2019

(65) Prior Publication Data
US 2021/0363126 A1    Nov. 25, 2021

(30) Foreign Application Priority Data
Oct. 14, 2017  (IN) .............................. 201721036571

(51) Int. Cl.
*C07D 317/60* (2006.01)

(52) U.S. Cl.
CPC .................................. *C07D 317/60* (2013.01)

(58) Field of Classification Search
CPC ..................................................... C07D 317/60
USPC ......................................................... 549/435
See application file for complete search history.

(56) References Cited

U.S. PATENT DOCUMENTS

| 4,209,446 A * | 6/1980 | Schulze ............... C07D 317/60 540/596 |
| 5,744,161 A | 4/1998 | Majeed et al. |
| 6,054,585 A | 4/2000 | Majeed et al. |
| 6,365,601 B1 | 4/2002 | Gaikar et al. |

FOREIGN PATENT DOCUMENTS

| CN | 104311530 A | 1/2015 |
| EP | 0 002 734 A2 | 12/1978 |

\* cited by examiner

*Primary Examiner* — Kristin A Vajda
(74) *Attorney, Agent, or Firm* — Kramer & Amado, P.C.

(57) ABSTRACT

The present application relates to a process for the preparation of piperine of high purity having low concentrations of isomeric impurities.

20 Claims, 3 Drawing Sheets

PROCESS FOR THE PREPARATION OF PIPERINE

TECHNICAL FILED

The present invention relates to substantially pure piperine and an improved process for the preparation of piperine. More specifically, the invention provides a process for the preparation of substantially pure piperine, having low concentrations of isomeric impurities.

BACKGROUND OF THE INVENTION

Piperine, the technical grade active ingredient, is naturally occurring in the black pepper plant, Piper nigrum L. The amount of piperine varies in plants belonging to the Piperaceae family; it constitutes 2% to 7.4% of both black pepper and white pepper (Piper nigrum L.; Ravindran 2003; Peter 2006; Parthasarathy and others 2008), although some reports pointed to higher piperine content of black pepper up to 9% (Gaikar and Raman 2002; Agarwal 2010), 4% of long pepper (Piper longum L.) fruits, and 4.5% of Balinese long pepper fruits (Piper retrofractum Vahl; Gaikar and Raman 2002). The piperine content of pepper can be influenced by many environmental factors including climate, growing conditions, and its place of origin (Peter 2006).

Piperine, as the most abundant alkaloid in pepper, was first isolated from the extract of pepper by Hans Christian Ørsted in 1819. It was extracted as a yellow crystalline compound with a melting point of 128 to 130° C. The chemical structure of piperine was later identified as piperoylpiperidine, with the chemical formula of $C_{17}H_{19}NO_3$, and with the IUPAC name 1-(5-[1,3-benzodioxol-5-yl]-1-oxo-2,4-pentadienyl) piperidine.

Piperoylpiperidine (piperine) exists as 4 isomeric structures: piperine (trans-trans isomer)(I), isopiperine (cis-trans isomer), chavicine (cis-cis isomer), and isochavicine (trans-cis isomer), as illustrated in FIG. 1; however, the 3 geometric isomers isopiperine, chavicine and isochavicine have almost no pungency.

Figure 1

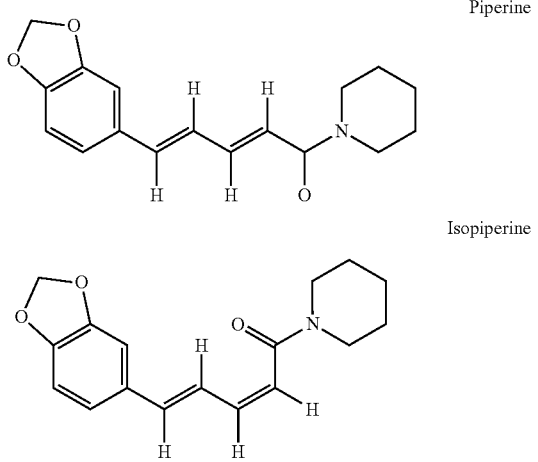

Piperine

Isopiperine

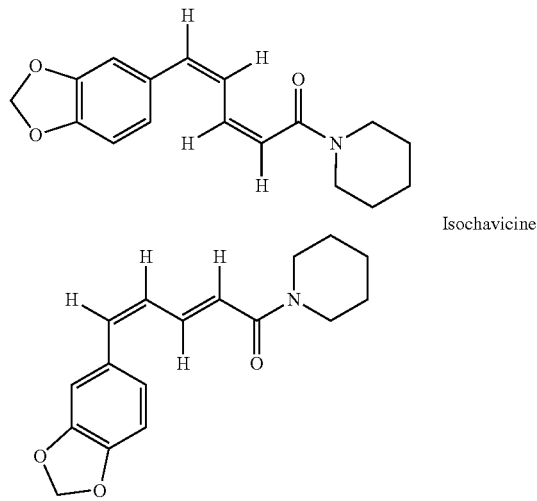

Chavicine

Isochavicine

Piperine has been used in herbal medicine as an anti-inflammatory, anti-arthritic, and anti-depressant. Moreover, it has been reported to act as a bioenhancer, a compound used in combination with a pharmaceutical in order to increase drug bioavailability, in combination with propranolol, theophylline, ciprofloxacin, and tetracycline. Recently, piperine was used as a bioenhancer with the antitubercular drug, rifampicin. The combined therapy of the drug with piperine has enabled the therapeutic dose of rifampicin by 50%.

Various process are disclosed in the prior art to obtain high purity piperine.

U.S. Pat. No. 5,744,161 teaches an extraction process of piperine from black pepper, having assay by HPLC 98%. Isolatation of piperine from a suitable oleoresin material obtained from the fruit or plant of the Piperaceae family is disclosed.

U.S. Pat. No. 6,054,585 discloses a process to recover piperine from resin of black pepper, wherein a mixture of 0.9 kg of urea, and 0.3 kg of resin of black pepper are refluxed in ethanol or methanol, the resultant filtrate is concentrated to yield piperine and some unreacted urea, which is further recrystallized to yield 75 g of 98% pure piperine.

U.S. Pat. No. 6,365,601 discloses a two-step process for the extraction of piperine from plants of piper species using aqueous hydrotrope solution. The isolated piperine has recovery of 58.8% (716 mg.) based on the amount of piperine present in the dried fruit with a purity of 98%.

Linchan Huaxue Yu Gongye (2008), 28(2), 6-10 discloses Preparative separation and purification of piperine from Piper nigrum Linn. by high-speed counter-current chromatography with a 2-2-phase solvent system composed of petroleum ether (60-90° C.)-Ethyl acetate-methanol-water (1:0.8:1:0.8, vol. ratio), wherein pieperine is obtained at 99.1% purity.

CN 104311530 A discloses a method of extracting high purity piperine comprising (1) grinding pepper fruit to obtain 60 mesh powder, adding 95% ethanol soln., immersing for 0.5 h, refluxing in 80° C. water bath for 2 h, collecting the filtrate and the filter residue, (2) vacuum distilling and concentrating the filtrate, (3) immersing the filter residue in 95% ethanol for 0.5 h, refluxing, vacuum filtering, collecting the filtrate, (4) combining the filtrate, vacuum distilling and concentrating, (5) regulating pH to 4 with 6.0 mol/L HCl, stewing for 4 h, centrifugating for 10 min, removing the undissolved substance, (6) regulating pH to 11 with 10% sodium hydroxide, (7) adding distilled water, cooling for 4 h, (8) centrifugating at 1200 rpm for 10 min to obtain crude piperine, (9) recrystallizing the crude piperine in acetone for 2-3 times, and (10) washing the obtained solid with ethyl ether, and vacuum drying to obtain high-purity piperine with a content of 98.9% and a purity of 99.96%. However, the process disclosed is not only cumbersome but also there is no enabling disclosure.

The processes disclosed in the prior art suggest extraction of *Piper nigrum* oleoresin containing piperine and other volatile oils using large volume of solvents. Piperine containing oleoresin is then solvent extracted and recrystallized to obtain pure piperine. Further, the extraction process is not selective as other compounds like gums, polysaccharides and resins are also extracted together reducing the purity of piperine. Hence, requires repetitive recrystallization to obtain piperine with a maximum purity of 99.1%. Thus, the post extraction processing to purify piperine is cumbersome and uneconomical. These conventional processes are carried out using several steps which often present difficult operating conditions and result in a high cost of production.

An alternative synthetic route is disclosed in number of literature which involves a Wittig-Horner reaction of piperonal (II) with an appropriate phosphorane. The complete synthesis is shown below in scheme 1.

The boiling points of the two compounds are nearly the same, so it is not possible to separate them by distillation. The starting material used in this experiment, may contain as much as 15% of the 2(5H)-furanone which does not interfere with the reaction but might be present in the product as a significant impurity.

2. Triethyl phosphate has an extremely disagreeable odour. Because of the exothermic reaction at high temperature of 120-130° C., the toxicity of ethyl bromide and the stench of triethylphosphite, this Wittig-Horner reaction should be carried out in a fume hood.

3. Excessive use of reagents for example piperidine 11 equivalents and sodium methoxide 4.5 equivalents.

4. Poor yield of 20% leads to high product cost thus not suitable for industrial scale up.

In another modification piperine is produced by reacting methyl-2-butanoate with NBS in the presence of CC14 and benzoyl peroxide to yield methyl 4-bromo-2-butenoate (VI). Wittig reaction of triethyl phosphite with the piperonal (III) to form the trans alkene, methyl piperate ((E, E)-5-(3,4-methylenedioxyphenyl)-2,4-pentadienoate) (VIII). Hydrolysis of the ester to piperic acid (VIIIA) and further condensation with piperidine using dry benzene and oxalyl chloride to yield piperine (I). This process also suffers from many disadvantages such as use of toxic and flammable CC14, benzoyl peroxide, carcinogenic benzene, oxalyl chloride and dimethoxyethane.

Scheme 1

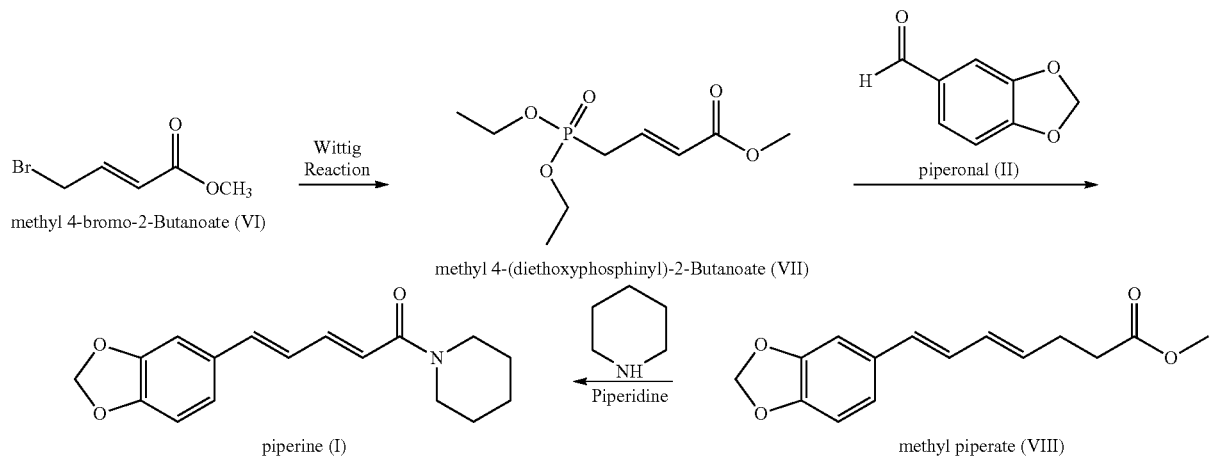

In the first Arbusov reaction, the phosphonate ester (VII) is prepared from methyl 4-bromo-2-Butanoate (VI) and triethylphosphite by reacting at 120-130° C. The product, methyl 4-(diethoxyphosphinyl)-2-Butanoate (VII), is reacted in the second step with freshly prepared sodium methoxide to generate the phosphonate carbanion in the presence of piperonal (III). The phosphonate carbanion undergoes a Wittig type reaction with the piperonal (III) to form the trans alkene, methyl piperate ((E, E)-5-(3,4-methylenedioxyphenyl)-2,4-pentadienoate) (VIII). Finally, reaction of methyl piperate (VIII) with piperidine in the presence of sodium methoxide in refluxing methanol solution for 40 hours gives piperine (I).

The process suffers many disadvantages.
1. Methyl 4-bromo-2-butenoate is very expensive and usually contaminated to some extent with 2(5H)-furanone, a side product of its synthesis and purification.

Further, the prior art processes are silent on the isomeric purity of the piperine. These patents/literature do not provide any insight about the presence of isomeric impurities as well as disclosure of any purity of the final product.

Owning to the broad spectrum of multiple uses of piperine, it would be a significant contribution to the art, to provide substantially pure piperine free from these and other impurities and processes for preparing such pure piperine which has high purity and high yield.

OBJECT OF THE INVENTION

An object of the invention is to provide substantially pure piperine.

Yet another object of the invention is to provide a process to prepare substantially pure piperine.

Yet another object of the invention is to provide a process to prepare substantially pure piperine, wherein piperine obtained is having purity of more than 99.5%.

Yet another object of the invention is to provide substantially pure piperine, wherein piperine obtained is having isomeric purity of more than 99.0%.

Yet another object of the present invention is to provide a process which is simple, economical and suitable for industrial scale up.

SUMMARY OF THE INVENTION

In line with the above objectives, the present invention provides a method for preparing substantially pure piperine of formula (I).

More preferably, the invention provides a synthetic method for preparing substantially pure piperine, which process comprises;
a) reacting crotonic acid (V) with a chlorinating agent to provide crotonoyl chloride (IV);
b) reacting crotonoyl chloride (IV) with piperidine to provide (2E)-1(1-piperidinyl)-2-buten-1-one (III); or
b') reacting methyl crotonate (IVA) with piperidine to provide (2E)-1(1-piperidinyl)-2-buten-1-one (III);
c) reacting (2E)-1(1-piperidinyl)-2-buten-1-one (III) with piperonyl aldehyde (II) in the presence of a suitable phase transfer catalyst to provide piperine having a purity of greater than 99.5%; and/or
d) optionally, crystallizing from a suitable solvent to get the piperine having desired purity.

In another aspect, the present invention provides substantially pure piperine having a purity of greater than 99.5%

In a further aspect, the present invention provides substantially pure piperine, having isomeric purity of more than 99.0%.

In a further aspect, the present invention provides substantially pure piperine, free from genotoxic impurities (GTIs).

In yet another aspect, the present invention provides pharmaceutical composition comprising substantially pure piperine.

In yet embodiment of the present invention, there is provided use of substantially pure piperine as a pharmacokinetic booster or enhancer to boost the effectiveness of the drugs.

Accordingly, there is provided a pharmaceutical composition comprising at least one drug and substantially pure piperine and use of the said composition for enhancing bioavailability, blood levels and efficacy of the drug.

DETAILED DESCRIPTION OF THE INVENTION

Figure 1:
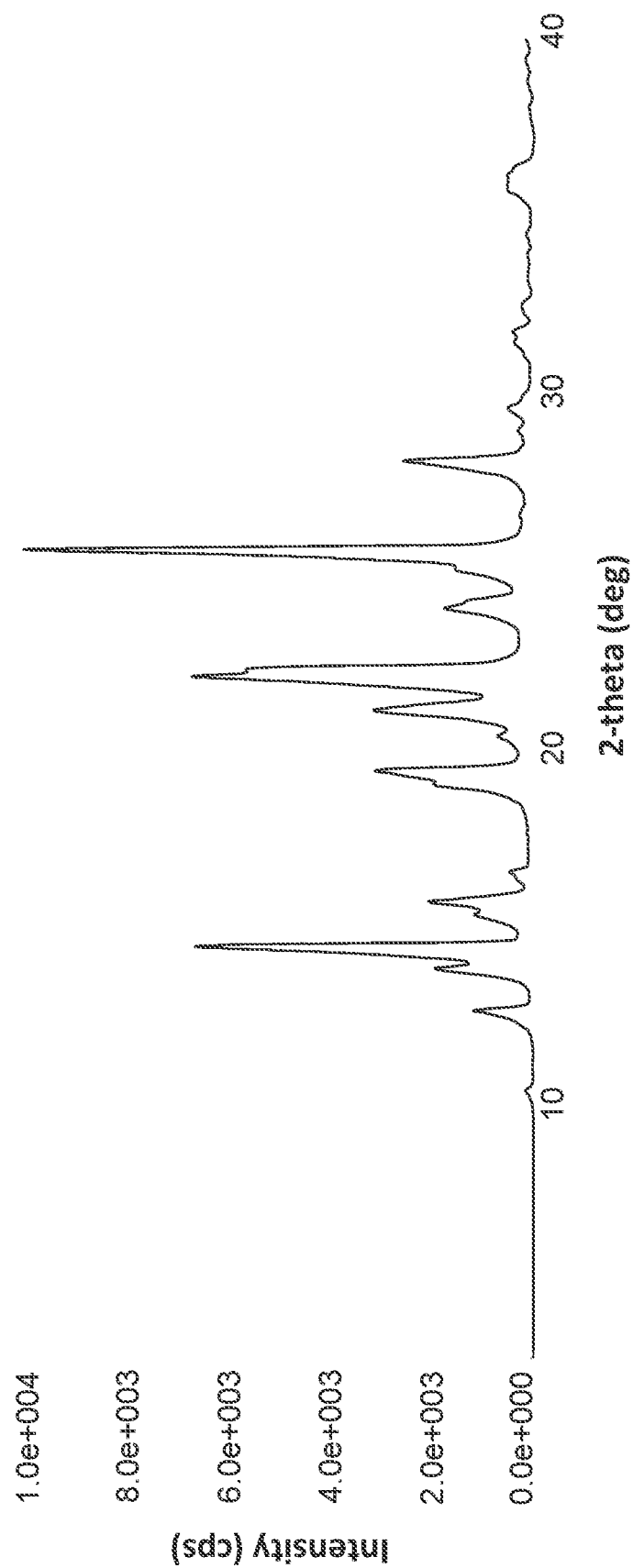
FIG. 1 shows a typical x-ray powder diffraction spectrum of crystalline solid of pure piperine

The present invention provides a process for the preparation of substantially pure piperine of Formula (I).

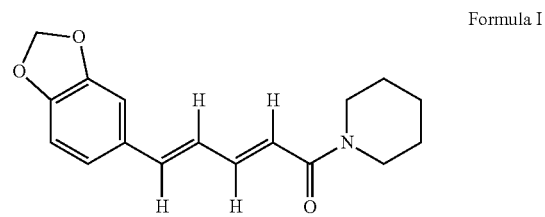 [SMILES: O=C(/C=C/C=C/c1ccc2c(c1)OCO2)N1CCCCC1]

Formula I

The term "substantially pure piperine" in the specification refers to piperine having purity (measured by HPLC) above 99.5%, preferably above 99.7%, and more preferably above 99.9%.

As used herein, the term "substantially pure" refers to a substance that has preferably between about 95% and 100% of one form (trans-trans isomer) and between about 5% and 0% of the other form, more preferably between about 99% and 100% of one form (trans-trans isomer) and between about 1% and 0% of the other form, and, most preferably, between about 99.9% and 100% of one form (trans-trans isomer) and about 0.1% and 0% of the other form.

In an embodiment, the present invention provides substantially pure piperine having purity (measured by HPLC) more than 99.5% and isomeric purity more than 99%.

In an embodiment, the process for the preparation of substantially pure piperine is as depicted below in scheme 2.

Scheme 2

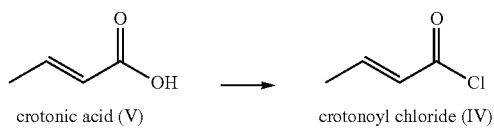

crotonic acid (V)     crotonoyl chloride (IV)

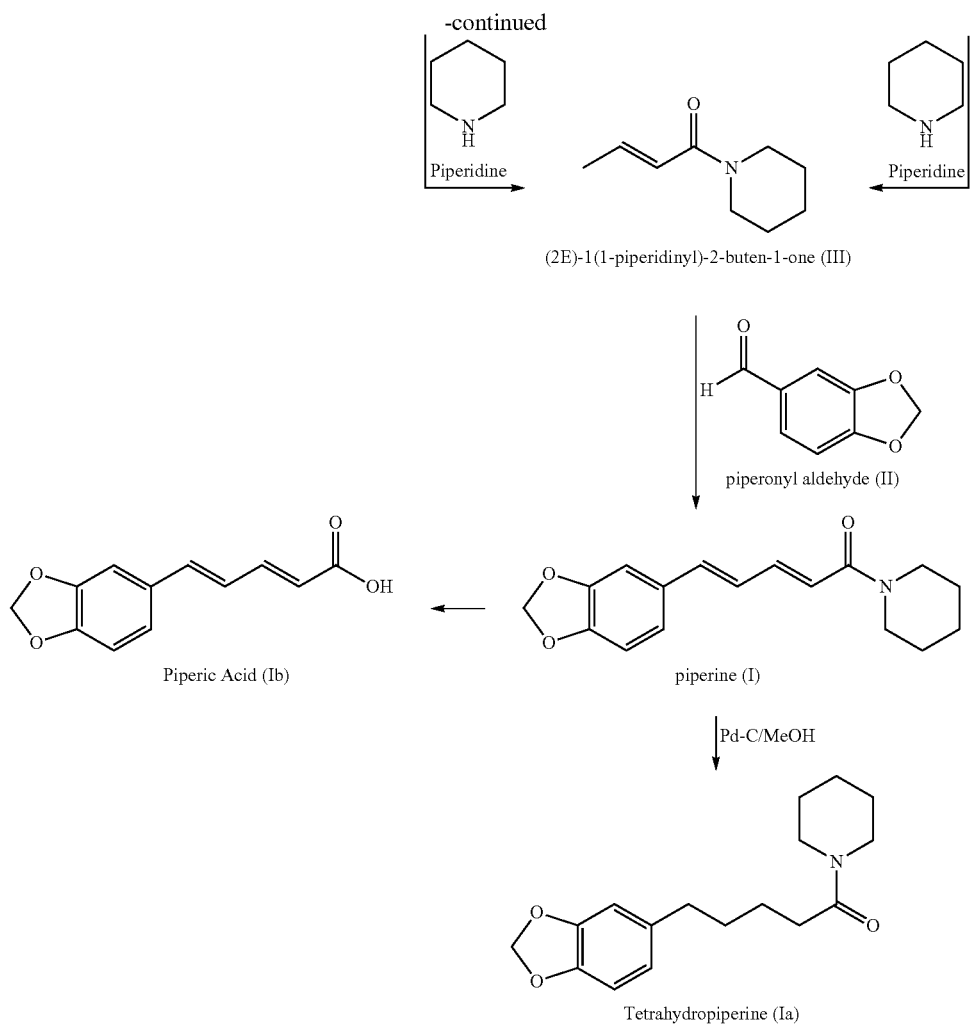

In an embodiment, crotonic acid is reacted with a chlorinating agent selected from thionyl chloride, oxalyl chloride, Phosphorous trichloride, Phosphorous pentachloride, Phosphorous oxychloride.

The chlorination reaction is preferably performed in the presence of a suitable solvent selected from alcohol (C1-4) or Ketones (C3-6) or organic solvents (C1-8 alkanes, dimethyl formamide, toluene, xylene) or halogenated organic solvents (Methylene dichloride, Ethylene dichloride) or Ethers (Methyl tertiary butyl ether, tetrahydrofuran, Di-isopropyl ether) or sulphoxides (dimethyl sulphoxide) or esters (Ethyl acetate, benzyl acetate, isoamyl acetate) or water or mixtures thereof; at a temperature ranging from about 0° C. to about 100° C., preferably about 10° C. to about 80° C., more preferably about 20° C. to about 50° C.; preferably, for about an hour to about 25 hours, more preferably about 10 hours to about 20 hours, most preferably about 12 hours to about 16 hours.

After completion of the reaction, the solvent is further distilled off to obtain crotonoyl chloride (IV).

The crotonoyl chloride (IV) is then reacted with piperidine to provide (2E)-1(1-piperidinyl)-2-buten-1-one (III). The reaction is preferably performed in the presence of a solvent at a temperature ranging from about 0° C. to about 50° C., preferably about 10° C. to about 40° C., more preferably about 20° C. to about 30° C.; preferably, for about an hour to about 25 hours, more preferably about an hour to about 20 hours, most preferably about an hour to about 10 hours.

Preferably the reaction mass is washed with first mixture of water and brine, then 5% dil HCl; followed by 5% sodium bicarbonate solution and washed with mixture of water and brine. The organic solvent is further distilled off to obtain (2E)-1(1-piperidinyl)-2-buten-1-one (III).

In one embodiment, condensation is carried out by isolating intermediate crotonoyl chloride (IV) and reacting with piperidine. In another embodiment, condensation is carried out in-situ without isolating the intermediate crotonoyl chloride (IV).

Alternately, methyl crotonate (IVA) may be reacted with piperidine in the presence of suitable base to obtain (2E)-1 (1-piperidinyl)-2-buten-1-one (III). Suitable base may be selected from organic and inorganic bases such as sodium methoxide, sodium t-butoxide, triethylamine, diisoproylamine and the like.

The reaction is preferably performed in the presence of a suitable solvent selected from polar and nonpolar solvents; at a temperature ranging from about 0° C. to about 100° C., preferably about 10° C. to about 80° C., more preferably at about 30° C. to about 60° C.; preferably, for about an hour to about 25 hours, more preferably about 10 hours to about 20 hours, most preferably about 12 hours to about 16 hours.

In an embodiment, (2E)-1(1-piperidinyl)-2-buten-1-one (III) is reacted with piperonyl aldehyde (II) in the presence of a suitable phase transfer catalyst to provide piperine (I). The pH of the reaction mass is maintained by using a suitable base. The base can be selected from the group consisting of one or more of alkali metal hydroxide, metal amides, metal alkoxides, amine bases, and alkali metal hydrides.

Examples of suitable bases are: sodium hydroxide, potassium hydroxide, sodium hydride, potassium hydride, sodium amide, lithium diisopropylamide, lithium hexamethyldisilazide, sodium methoxide, sodium ethoxide and potassium t-butoxide. Most preferably, the base is selected from the group consisting of sodium hydroxide and potassium hydroxide. Preferably, aqueous base such as aqueous NaOH/KOH solution is added over a period of 30 mins to 1 hour.

Suitable phase transfer catalyst is selected from benzyl triethyl ammonium chloride, tetrabutyl ammonium bromide, aliquat 336, benzyl trimethyl ammonium chloride, methyl tricapryl ammonium chloride, methyl tributyl ammonium chloride, and methyl trioctyl ammonium chloride or mixtures thereof.

The reaction is preferably performed in the presence of a suitable solvent selected from DMSO, DMF, or mixtures thereof; at a temperature ranging from about 0° C. to about 50° C., preferably about 10° C. to about 40° C., more preferably about 20° C. to about 30° C.; preferably, for about an hour to about 25 hours, more preferably about 10 hours to about 20 hours, most preferably about 10 hours to about 15 hours.

In an embodiment piperine is optionally purified in the suitable solvent or solvents mixture thereof. A suitable solvent is selected from polar solvent and nonpolar solvents selected form toluene, ethanol, IPA, ethyl acetate, acetone and mixture thereof.

The purity (measured by HPLC) of the piperine obtained according to the present invention is preferably about above 99%, more preferably about above 99.5% and still more preferably about above 99.9%; and contains the isomeric impurities isopiperine, chvicine and isochavicine below detection limit and meeting the ICH guidelines.

In yet another embodiment of the invention related to a process for the preparation of substantially pure piperine, wherein substantially pure piperine contains the genotoxic impurities, such as shown below in scheme 3, Scheme 3

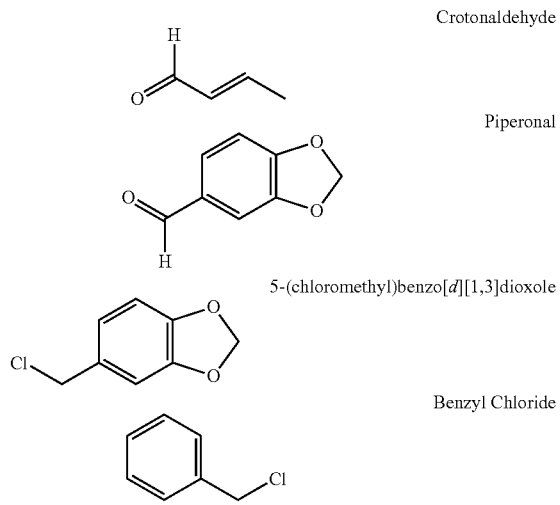

Crotonaldehyde

Piperonal 5-(chloromethyl)benzo[d][1,3]dioxole

Benzyl Chloride

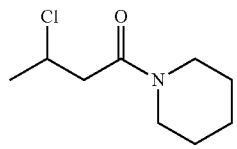

3-chlora-1-(piperidin-1-yl)butan-1-one individually and collectively below 50 ppm thereby meeting the ICH guidelines. The piperine obtained by the process of the present invention is further characterized by XRD, which is found to be substantially similar with crystalline Form I of piperine.

Figure 2:
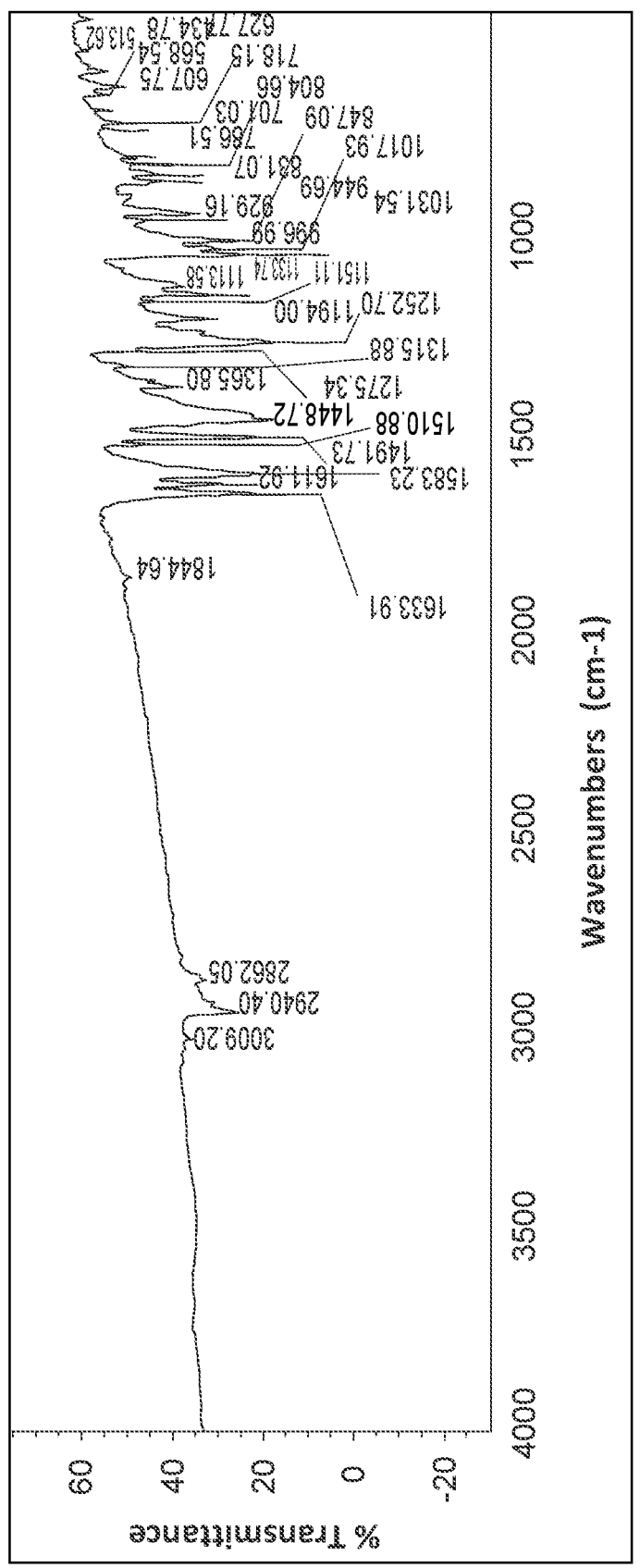
FIG. 2 shows a FTIR spectrum of crystalline solid of pure piperine
Figure 3:
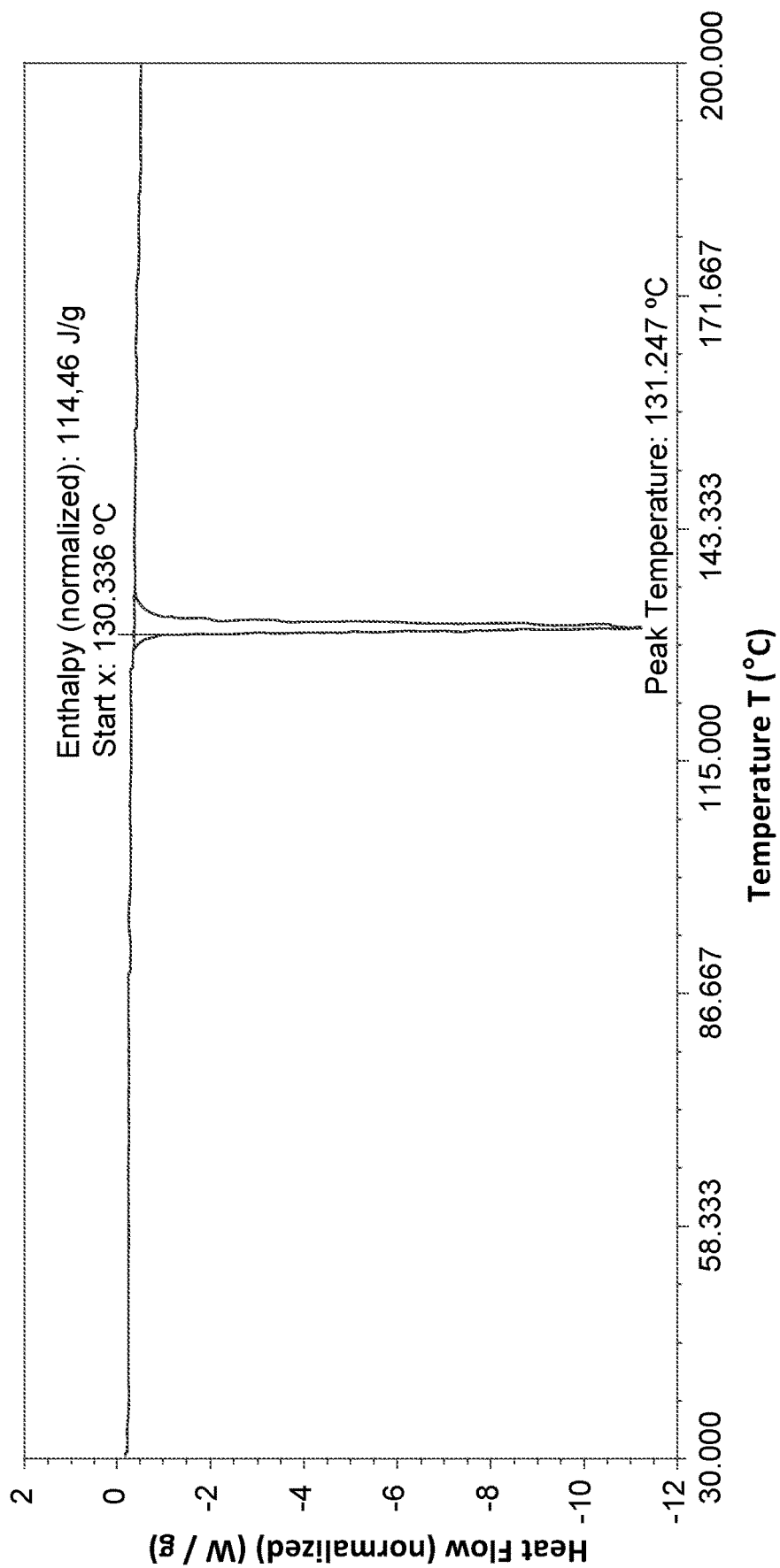
FIG. 3 shows a Differential Scanning calorimetry (DSC) thermogram of crystalline solid of pure piperine

In an embodiment crystalline Form I of piperine is characterised by
a) X-ray powder diffraction(XRPD) pattern substantially as shown in FIG. 1;
b) IR substantially as shown in FIG. 2; and
c) DSC substantially as shown in FIG. 3.

In an embodiment, piperine obtained by the process of the present invention is further hydrogenated to obtain tetrahydropiperine (Ia). The reaction is preferably carried out in the presence of a suitable catalyst, polar protic solvent and in the presence of a hydrogen source. Preferably, the catalyst is selected from Pd/C, Pt/C, PtO2, Ru and the like. Preferably, the polar protic solvent is selected from the group consisting of a C1-C5 alcohol (such as methanol, ethanol, isopropanol, butanol, and tert-butanol), acetonitrile, water, and mixture thereof. Most preferably, the solvent is methanol.

In an embodiment, piperine obtained by the process of the present invention is further hydrolysed to piperic acid (Ib). The hydrolysis is preferably performed using an aqueous acid or aqueous base solution in the presence of a suitable solvent.

The process of the present invention is advantageous over prior art processes as the reaction steps are conducted at low temperature, reduces reaction hours, minimises large handling of reaction solvents and thus making it economical for industrial scale up.

Other features and embodiments of the invention will become apparent by the following examples which are given for illustration of the invention rather than limiting its intended scope. Various changes and modifications to the disclosed embodiments will be apparent to those skilled in the art.

EXAMPLE

Example 1

Preparation of (E)-1-(Piperidin-1-yl) but-2-en-1-one (III)

To a well stirred mixture of crotonic acid (100 gms, 1.16 moles) DMF (1.0 ml) in dichloromethane 500 ml was added thionyl chloride (100 ml, 1.34 moles) dropwise under N₂ atmosphere at 25-30° C. and stirred for 14 hours at 30-35° C. After completion, reaction mass was concentrated and diluted with MDC (1000 ml) and cooled to 0° C. Piperidine (310.0 ml, 3.15 moles) was added drop wise over a period of 3 hours below 10° C. The reaction mixture was then agitated at 25-30° C. for 7 hrs. After completion, the reaction mixture was filtered and filtrate was sequentially washed with water (2×500 ml), 5% dil HCl 500 ml, 5% sodium bicarbonate (500 ml) and finally with brine solution (500 ml). Organic layer was evaporated to obtain title compound as dark brown colored oil.

Yield: 110.0 gms
HPLC Purity: 95%

Example 2

Preparation of (E)-1-(Piperidin-1-yl)but-2-en-1-one (III)

To a well stirred mixture of crotonic acid (50 gms, 0.580 moles) DMF (1.0 ml) in toluene (500 ml) was added thionyl chloride (50 ml, 0.670 moles) dropwise under $N_2$ atmosphere at 25-30° C. and stirred for 10 hours at 35-40° C. After completion of the reaction additional 250 ml toluene is added to reaction mass. Piperidine (150.0 ml, 0.500 moles) was added drop wise over a period of 3 hours below 10° C. The reaction mixture was then agitated at 25-30° C. for 7 hrs. The progress of the reaction was monitored by HPLC. After completion, the reaction mixture was filtered and filtrate was sequentially washed with water (2×250 ml), 5% dil HCl (250 ml), 5% Sodium bicarbonate (250 ml) and finally with brine solution (250 ml). Organic layer was evaporated to obtain title compound as dark brown colored oil.

Yield: 65.0 gms
HPLC Purity: 95%

Example 3

Preparation of Piperine (I)

To a well stirred mixture of (E)-1-(Piperidin-1-yl) but-2-en-1-one (100.0 gm, 0.653 moles), benzyl triethyl ammonium chloride (27.0 gm, 0.118 moles) in DMSO (1000 ml) was added piperonyl aldehyde (88.0 gm, 0.586 moles) at 25-30° C. Aq. NaOH (4.7 gm 0.118 moles in 100 ml water) was added drop wise over a period of 45 min. The reaction mixture was then stirred at 25-30° C. for 12-15 hours. After completion of reaction it was quenched in water (5000 ml) and further stirred at 25° C. for 2.0 hrs. The precipitated solid was isolated by filtration, washed with water and dried under vacuum at 55-60° C. to yield title compound piperine as yellow solid.

The crude piperine was purified by crystallization from 500 ml toluene to obtain crystalline solid.

Yield: 89.0 gm.
HPLC Purity: 99.95%

Example 4

Preparation of Tetrahydro Piperine (Ia)

To a 1.0 lit hydrogenator, piperine (15.0 gms, 0.052 moles) along with methanol (140 ml) was charged at 25-30° C. In another beaker slurry of 10% Pd/C (1.5 gm, 50% wet) in 10.0 ml of methanol was prepared and charged into above reaction mass at 25-30° C. The hydrogen pressure (40-50 PSI) was applied and maintained reaction at 40-45° C. for 10-12 hrs. Reaction mixture was cooled to 25-30° C. and filtered through hyflo to remove catalyst and the bed was washed with methanol (15 ml). Distilled out methanol under vacuum below 45° C. Added n-Heptane (100 ml) and stirred for 12-13 hrs. The precipitated solid was isolated by filtration, washed with n-Heptane and dried under vacuum at 35-40° C. to obtain title compound tetrahydropiperine as white solid.

Yield: 14.0 gms,
Purity: 99.5%

Example 5

Preparation of Piperic Acid (Ib)

Charged piperine (15.0 gm, 0.052 moles) with ethylene glycol (150 ml) at 25-30° C. into reaction flask, added potassium Hydroxide (13.3 gm, 0.238 moles) at 25-30° C. Temperature of the reaction was increased to 115° C. and maintained for 14-15 hrs. After completion of reaction, the reaction mixture was cooled to 15-20° C. and added water (150 ml) into reaction mixture followed by acidification with 15.0 ml of Conc. HCl. Reaction mixture was stirred further for 1.0 hr at 15-20° C. and the precipitated solid was filtered, washed with water. Wet cake was charged into reaction flask along with methanol (55 ml) and stirred for 1.0 hr. at 25-30° C. The solid was isolated by filtration, washed with 15 ml of methanol and under vacuum at 25-30° C. to give title compound piperic acid.

Yield: 7.0 gm.
HPLC Purity: 96.5%

Example 6

Preparation of (E)-1-(Piperidin-1-yl)but-2-en-1-one (III)

To a well stirred mixture of sodium methoxide (16.2 gm, 0.300 mole) in toluene (400 ml) was added under piperidine (40 gms, 0.405 mole) under nitrogen atmosphere at room temperature. The temperature was increased to 55° C. and stirred for 1 hr and then added methyl crotonate (50 gms, 0.500 mole) dropwise within a period of 30 min. The reaction mixture was stirred further at 55-60° C. for 12 to 15 hrs and then cooled to room temperature. The reaction mixture was quenched with water (500 ml). The organic layer was separated and washed with water and brine solution and concentrated to obtain title compound.

Yield: 41 gms
HPLC Purity~50%.

Example 7

Preparation of (E)-1-(Piperidin-1-yl)but-2-en-1-one (III)

To a well stirred mixture of crotonic acid (100 gms, 1.16 moles) DMF (2.0 ml) in toluene (3000 ml) was added thionyl chloride (200 ml, 1.387 moles) dropwise under $N_2$ atmosphere at 25-35° C. and stirred for 2 hours at 35-40° C. After completion of the reaction, the reaction mixture was cooled to 5-10° C. Piperidine (690.0 ml, 2.3 moles) was added drop wise over a period of 3 hours below 10° C. The reaction mixture was then agitated at 25-30° C. for 1 hr. The progress of the reaction was monitored by TLC. After completion, the reaction mixture was diluted with water (1400 ml) and stirred at 25-30° C. for 15-20 min. The organic layer separated, washed with water (1400 ml), 5% dil HCl (1400 ml), 5% Sodium bicarbonate (1400 ml) and finally with water (1400 ml). Organic layer was evaporated to obtain title compound as oil.

Yield: 240 gms

Example 8

Preparation of Piperine (I)

To a well stirred mixture of (E)-1-(Piperidin-1-yl) but-2-en-1-one (225.0 gm, 1.468 moles), benzyl triethyl ammonium chloride (67.0 gm, 0.294 moles) in DMSO (2250 ml) was added piperonyl aldehyde (198.5 gm, 1.322 moles) at 25-30° C. The reaction mixture was stirred for 15-20 mins and aq. NaOH (24.0 gm 0.6 moles in 225 ml water) was added drop wise over a period of 45 min. The reaction mixture was then stirred at 25-30° C. for 5 hours. After completion of reaction it was quenched in water (6750 ml) and further stirred at 25° C. for 1.0 hr. The precipitated solid was isolated by filtration, washed with water and dried under vacuum at 55-60° C. to obtain title compound piperine as yellow solid.

Yield: 301.0 gm

Toluene Purification:

The crude piperine (265 gm) was dissolved in 2650 ml toluene at 45-50° C. Treated with charcoal 926.5 gm) for 30 min at 45-50° C. The reaction mixture was filtered and the clear filtrate was evaporated to obtain residue. The residue was stirred in 1060 ml toluene at 60-65° C. for 30 min. The reaction mixture was cooled to 25-30° C. and further chilled to 0-5° C. and stirred for 1 hr. The precipitated solid was isolated by filtration, and dried under vacuum at 55-60° C. for 12-15 hrs to obtain title compound Piperine as yellow solid.

Yield: 210 gm

HPLC Purity: 99.6%

Other isomers<0.02%

Ipa Purification:

Piperine (180 gm) was dissolved in 1440 ml IPA at 60-65° C. The reaction mixture was stirred for 30 mins, gradually cooled to 25-30° C. and further chilled to 0-5° C. and stirred for 1 hr. The precipitated solid was isolated by filtration, and dried under vacuum at 55-60° C. for 12-15 hrs to obtain title compound Piperine as yellow solid.

Yield: 145 gm

HPLC Purity: 99.95%

Other isomers<0.02%

We claim:

1. A process for the preparation of piperine of Formula (I), comprising:

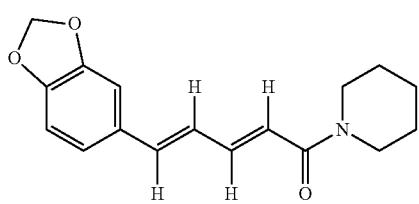

(I)

a) preparing (2E)-1(1-piperidinyl)-2-buten-1-one of formula (III) by reacting methyl crotonate (IVA) with piperidine and a first base to provide (2E)-1(1-piperidinyl)-2-buten-1-one (III), the first base being an amine or a metal alkoxide; and

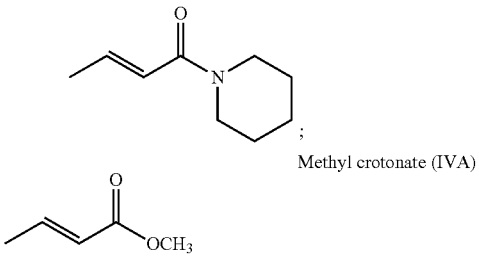

(2E)-1(1-piperidinyl)-2-buten-1-one (III)

Methyl crotonate (IVA)

b) reacting (2E)-1(1-piperidinyl)-2-buten-1-one of formula (III) with piperonyl aldehyde of formula (II) in the presence of a phase transfer catalyst to provide piperine:

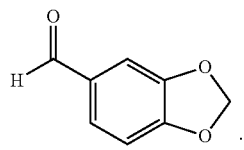

piperonyl aldehyde (II)

2. The process of claim 1, further comprising crystallizing the piperine from a crystallization solvent to obtain the piperine in a desired purity.

3. The process of claim 1, further comprising crystallizing the piperine from a crystallization solvent selected from the group consisting of toluene, ethanol, IPA, ethyl acetate acetone and mixture thereof.

4. The process of claim 1, wherein (2E)-1(1-piperidinyl)-2-buten-1-one of formula (III) is reacted with piperonyl aldehyde of formula (II) in the presence of a solvent selected from the group consisting of DMSO, DMF, and a mixtures thereof.

5. The process of claim 1, wherein (2E)-1(1-piperidinyl)-2-buten-1-one of formula (III) is reacted with piperonyl aldehyde of formula (II) at a temperature ranging from about 0° C. to about 50° C.

6. The process of claim 1, wherein the phase transfer catalyst is selected from the group consisting of benzyl triethyl ammonium chloride, tetrabutyl ammonium bromide, N-Methyl-N,N,N-trioctylammonium chloride, benzyl trimethyl ammonium chloride, methyl tricapryl ammonium chloride, methyl tributyl ammonium chloride, methyl trioctyl ammonium chloride, and a mixture thereof.

7. The process of claim 1, wherein the first base is selected from the group consisting of sodium methoxide, sodium t-butoxide, triethylamine, diisoproylamine, and mixtures thereof.

8. The process of claim 1, wherein methyl crotonate (IVA) is reacted with piperidine at a temperature ranging from about 0° C. to about 100° C.

9. The process of claim 1, wherein methyl crotonate (IVA) is reacted with piperidine in the presence of a second base selected from the group consisting of an alkali metal hydroxide, a metal amide, a metal alkoxide, an amine base, an alkali metal hydride, and a mixture thereof.

10. A process for the preparation of piperine of Formula (I), comprising:

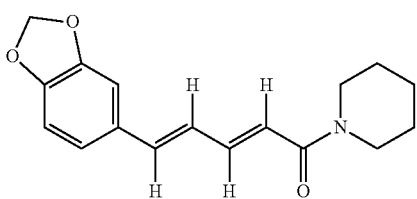

(I)

a) preparing (2E)-1(1-piperidinyl)-2-buten-1-one of formula (III) by reacting crotonic acid of Formula (V) with a chlorinating agent to provide a reaction mixture containing crotonoyl chloride of formula (IV),
b) adding piperidine to the reaction mixture without isolating the crotonoyl chloride to provide (2E)-1(1-piperidinyl)-2-buten-1-one of formula (III); and

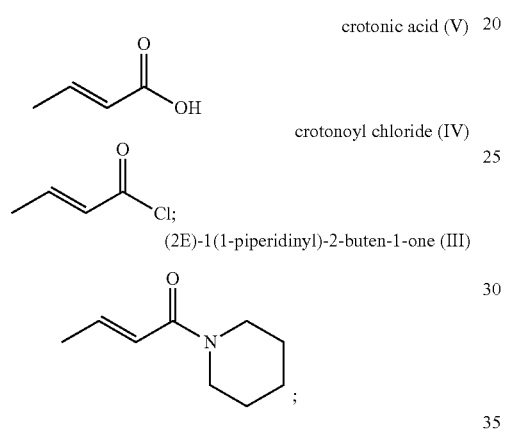

crotonic acid (V)

crotonoyl chloride (IV)

(2E)-1(1-piperidinyl)-2-buten-1-one (III)

c) reacting (2E)-1(1-piperidinyl)-2-buten-1-one of formula (III) with piperonyl aldehyde of formula (II) in the presence of a phase transfer catalyst to provide piperine:

piperonyl aldehyde (II)

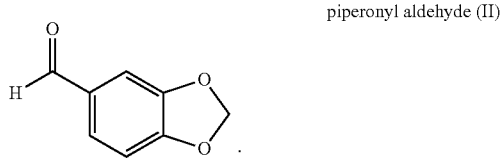 [SMILES: O=Cc1ccc2c(c1)OCO2]

11. The process of claim 10, wherein the chlorinating agent is selected from the group consisting of thionyl chloride, oxalyl chloride, phosphorous trichloride, phosphorous pentachloride, Phosphorous oxychloride, and a mixture thereof.

12. The process of claim 10, wherein the crotonic acid of Formula (V) is reacted with the chlorinating agent in the presence of a solvent selected from the group consisting of C1-C4 alcohols, C3-C6 ketones, C1-C8 alkanes, dimethyl formamide, toluene, xylene, halogenated organic solvents, ethers, sulphoxides, esters, water and mixtures thereof.

13. The process of claim 10, wherein the crotonic acid of Formula (V) is reacted with the chlorinating agent in the presence of a solvent selected from the group consisting of methylene dichloride, ethylene dichloride, methyl tertiary-butyl ether, tetrahydrofuran, diisopropyl ether, dimethyl sulphoxide, ethyl acetate, benzyl acetate, isoamyl acetate, water, and mixtures thereof.

14. The process of claim 10, wherein the crotonic acid of Formula (V) is reacted with the chlorinating agent at a temperature ranging fro n about 0° C. to about 100° C.

15. The process of claim 10, wherein the phase transfer catalyst is selected from the group consisting of benzyl triethyl ammonium chloride, tetrabutyl ammonium bromide, N-Methyl-N,N,N-trioctylammonium chloride, benzyl trimethyl ammonium chloride, methyl tricapryl ammonium chloride, methyl tributyl ammonium chloride, methyl trioctyl ammonium chloride, and a mixture thereof.

16. The process of claim 10, wherein the crotonoyl chloride (IV) is reacted with piperidine at a temperature ranging from about 0° C. to about 50° C.

17. A process of making tetrahydropiperine of formula (Ia), comprising:

Tetrahydropiperine (Ia)

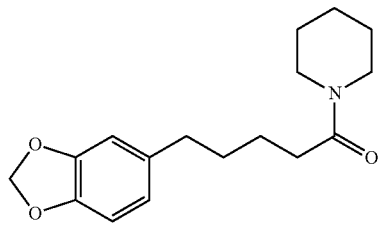

making piperine of formula (I) by the process of claim 1, and
hydrogenating the piperine with hydrogen in the presence of a catalyst.

18. A process of making piperic acid of formula (Ib), comprising:

Piperic Acid (Ib)

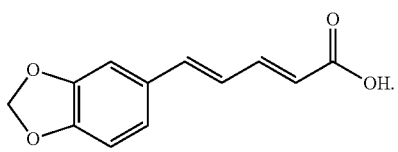

making piperine of formula (I) by the process of claim 10, and
hydrolyzing the piperine to produce the piperic acid.

19. A process of making tetrahydropiperine of formula (Ia), comprising:

Tetrahydropiperine (Ia)

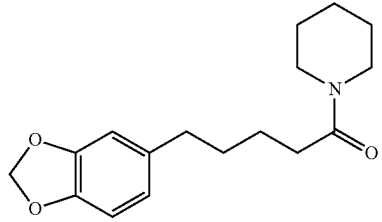

making piperine of formula (I) by the process of claim 1, and
hydrogenating the piperine with hydrogen in the presence of a catalyst.

20. A process of making piperic acid of formula (Ib), comprising:
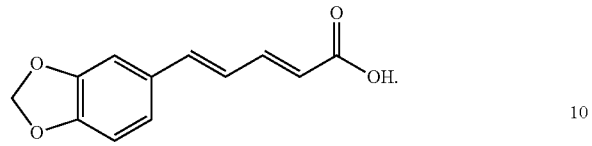
Piperic Acid (Ib)
making piperine of formula (I) by the process of claim 10, and
hydrolyzing the piperine to produce the piperic acid.
* * * * *